United States Patent
Schultz et al.

(10) Patent No.: US 6,428,580 B2
(45) Date of Patent: *Aug. 6, 2002

(54) USE OF ASCORBIC ACID IN PERMANENT WAVING AND HAIR COLORING COMPOSITIONS

(75) Inventors: Thomas Schultz, Randolph; Natalya Fadeeva, Clark, both of NJ (US); David W. Cannell, New York, NY (US)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/915,320

(22) Filed: Aug. 20, 1997

(51) Int. Cl.$^7$ ............................. A61K 7/13; A61K 7/135
(52) U.S. Cl. .................. 8/406; 252/186.29; 252/186.31
(58) Field of Search ............................. 8/406, 431, 111; 510/311, 376, 378; 252/186.27, 186.28, 186.29, 186.3, 186.31, 186.32, 186.43

(56) References Cited

U.S. PATENT DOCUMENTS

| | | | | |
|---|---|---|---|---|
| 2,780,579 A | | 2/1957 | Schwarz et al. | 167/87.1 |
| 3,065,139 A | * | 11/1962 | Ericsson et al. | 424/613 |
| 3,632,295 A | * | 1/1972 | Hall | 8/111 |
| 3,910,289 A | | 10/1975 | Wajaroff et al. | 132/205 |
| 4,311,598 A | * | 1/1982 | Verachtert | 210/757 |
| 4,664,847 A | * | 5/1987 | Williams | 512/4 |
| 5,032,138 A | | 7/1991 | Wolfram et al. | 8/412 |
| 5,037,634 A | * | 8/1991 | Williams et al. | 424/49 |
| 5,080,090 A | | 1/1992 | Liau et al. | 601/134 |
| 5,270,337 A | | 12/1993 | Graf | 514/499 |
| 5,373,025 A | * | 12/1994 | Gay | 514/642 |
| 5,525,123 A | | 6/1996 | Lorenz et al. | 8/408 |
| 5,622,646 A | * | 4/1997 | Scialla et al. | 252/186.33 |
| 5,646,271 A | * | 7/1997 | Stehlin et al. | 536/123.1 |
| 5,660,862 A | * | 8/1997 | Park et al. | 424/616 |
| 5,686,014 A | * | 11/1997 | Baillely et al. | 252/186.33 |

FOREIGN PATENT DOCUMENTS

| | | | |
|---|---|---|---|
| DE | 1617829 | | 4/1972 |
| DE | 3642 097 | | 6/1988 |
| EP | 0 401 454 | | 12/1990 |
| EP | 0 642 783 | | 3/1995 |
| GB | 760 659 | | 11/1956 |
| GB | 1099105 | | 1/1968 |
| GB | 2003033 | | 3/1979 |
| GB | 2210627 | | 6/1989 |
| GB | 2264429 | * | 9/1993 |
| JP | 62-132813 | | 6/1987 |
| JP | 63-014712 | | 1/1988 |
| JP | 64-066109 | | 3/1989 |
| JP | 4-28372 | * | 1/1992 |
| WO | 9211042 | | 7/1992 |
| WO | 9404125 | | 3/1994 |
| WO | 95/05504 | * | 2/1995 |

OTHER PUBLICATIONS

English language Derwent Abstract of JP 4–28372, Toyo Ink Mfg Co., Jan. 1992.*
English language translation of FR 2,657,781, L'Oreal, pp. 1–31, Aug. 1991.*
Derwent Abstract of DE 36 42 097, Jun. 1988.
Derwent Abstract of EPO 0 401 454, Dec. 1990.
Derwent Abstract of DE 1617829, Apr. 1972.

* cited by examiner

*Primary Examiner*—John Hardee
(74) *Attorney, Agent, or Firm*—Finnegan, Henderson, Farabow, Garrett & Dunner, L.L.P.

(57) ABSTRACT

A novel oxidizing system comprising ascorbic acid, at least one metal ion and an oxidizing agent capable of generating an oxidizing potential of from about 100 to about 500 millivolts at a pH ranging from about 2 to about 10. The oxidizing system can be used in quenching or neutralizing permanent wave processes and in developing oxidative hair color.

19 Claims, No Drawings

USE OF ASCORBIC ACID IN PERMANENT WAVING AND HAIR COLORING COMPOSITIONS

FIELD OF THE INVENTION

The present invention relates to the use of ascorbic acid in hair care compositions, particularly in permanent waving and hair coloring compositions. More specifically, the invention relates to an oxidation system containing ascorbic acid, at least one metal ion, and an oxidizing agent which, when used in the inventive composition, is capable of generating an oxidizing potential of from about 100 to about 500 millivolts at a pH ranging from about 2 to about 10. The invention is also drawn to permanent waving and hair dyeing kits.

BACKGROUND OF THE INVENTION

In permanent hair waving, the hair is first treated with a reducing composition capable of breaking the disulfide bonds of the hair keratin (S—S) and causing the formation of sulfhydryl groups (—SH). In other words, the amino acid cystine in the hair is converted to cysteine. The hair is then re-shaped in a new form under applied mechanical tension, either by winding on rods (waving) or by combing through (straightening). The hair, while still under mechanical tension, is then subject to a neutralization step, during which the hair is treated with an oxidizing composition. The oxidizing composition causes the disulfide bonds of the hair keratin to be restored, i.e., reforming the amino acid cystine, and the hair now is capable of retaining the new configuration permanently.

The hair may be damaged if, during the neutralization step, hair is subjected to oxidants that are too strong. Over-oxidation generates cysteic acid instead of restoring the amino acid cystine. The presence of cysteic acid is undesirable because it does not allow the reformation of the disulfide bonds, resulting in weak, damaged hair.

In the art of permanent waving, the two most commonly used materials for quenching or neutralizing a permanent wave process are hydrogen peroxide and bromate salts. Each has its drawbacks. In permanent hair waving, the first step usually takes place at an alkaline pH of 7.5–10.0. The application of hydrogen peroxide, which is conventionally quite acidic, at pH 2.5–5.0, causes stress to the hair. Further, hydrogen peroxide may also "lift" the natural color of the hair and cause undesirable red undertones to develop. Bromate salts are used in some Asian countries as they will not redden hair like hydrogen peroxide. However, bromates are dangerous compounds in that they are explosive and ignitable.

Ascorbic acid, also known as Vitamin C, is widely used in the pharmaceutical industry and the cosmetic industry because of its biological activity. Attempts have also been made to use ascorbic acid in permanent waving of hair, both to break and to restore the disulfide bonds.

For example, in U.S. Pat. No. 2,780,579 to Schwartz et al., the oxidized form of ascorbic acid, i.e., dehydroascorbic acid (DHA), is taught as a perm neutralizer. The Schwartz et al. patent states that the powerful oxidants normally used in permanent waving, such as hydrogen peroxide, bromates, chlorates and chlorites, tended to over-oxidize the reduced hair. As a result, the oxidation goes beyond the cystine stage, resulting in irreversible damage to the hair. The over-oxidation renders the hair porous and brittle, and also causes hair discoloration. If lower concentrations of these oxidants are used, an insufficient disulfide bond recovery has been observed.

According to Schwartz et al., DHA is an effective oxidant, capable of converting cysteine back to the amino acid cystine in reduced hair without over-oxidizing the hair. Schwartz et al. used a mixture of ascorbic acid with hydrogen peroxide or other oxidants in the presence of buffers, forming DHA in situ.

Further, despite the statements in Schwartz et al. regarding the effectiveness of DHA, the reaction used therein is not much different from using peroxide alone. The molar ratio of ascorbic acid to hydrogen peroxide suggested in the examples of Schwartz was very high. This ratio was determined from Schwartz as follows:

(2 oz.×29 g/oz×6%*) /(34 g/mol)=0.1 mol hydrogen peroxide

*20 vol. hydrogen peroxide=6% by weight in water (0.25 g) /(176 g/mol)=0.0014 mol ascorbic acid.

RATIO=0.1 mol hydrogen peroxide/ 0.0014 mol ascorbic acid=72:1.

U.S. Pat. No. 5,270,337 to Graf teaches that the use of ascorbic acid and a divalent metal ion such as $Cu^{2+}$ can effectively remove oxygen from an aqueous solution by converting the oxygen to water. In Graf, ascorbic acid reduces $Cu^{2+}$ to $Cu^+$ to form DHA. $Cu^+$ (cuprous) ions form a complex with oxygen, and an electron transfer occurs to give $Cu^{2+}$ (cupric) ions and superoxide anion radicals. The radicals, in the presence of the copper, rapidly disproportionate into oxygen and hydrogen peroxide. The copper-ascorbate complex quickly reduces the hydrogen peroxide to water without the simultaneous production of oxygen or hydroxyl radicals.

Graf's invention is mainly used as a food preservative. Further, the copper-catalyzed degradation of peroxide taught in Graf does not solve the difficulty in the art of finding an effective peroxide-free permanent wave neutralizer and/or oxidation dye developing system.

Thus, it is desirable to develop an oxidizing system that would effectively restore disulfide bonds and/or develop oxidation hair color without using peroxides or bromates. In particular, it is desirable that the oxidizing system be able to accomplish this at a pH ranging from 5 to 10, preferably from pH 7.5 to 10.0. As discussed above, the first step in the permanent hair waving process usually takes place at a pH ranging from 7.5 to 10.0. The application of an oxidation solution in a similar pH range could be expected to be less stressful on the hair, as compared to the conventionally used hydrogen peroxide at a pH ranging from 2.5 to 5.0. In addition, such a system would be more compatible with oxidation hair dyes that are being developed in this same pH range, i.e., at a pH ranging from 7.5 to 10.0. Finally, this oxidation system would also provide for better color retention in tinted hair after permanent wave treatment.

Thus it was surprising and unexpected that the present invention, a system containing ascorbic acid, at least one metal ion catalyst, and an oxidizing agent capable of generating an oxidizing potential of from 100 to 500 millivolts at a pH ranging from 2 to 10 is an effective composition useful for application in place of peroxide for hair care applications.

SUMMARY OF THE INVENTION

To achieve these and other advantages, and in accordance with the purpose of the invention as embodied and broadly described herein, the present invention, in one aspect, provides an oxidizing system based on ascorbic acid and capable of effective restoration of disulfide bonds in reduced hair during the permanent wave process. The invention also provides an oxidizing system capable of developing color in oxidation dye systems. Further, the present invention provides an oxidizing system that does not render oxidative damage to the hair during permanent wave and/or color processing.

The present invention is thus drawn to an oxidizing system for application to keratinous substances, particularly human hair, the system containing ascorbic acid, at least one metal ion, and an oxidizing agent capable of generating an oxidizing potential of from about 100 to about 500 millivolts wherein the system has a pH ranging from about 2 to about 10.

The present invention is also directed to a method for using this oxidizing system to neutralize or "quench" a permanent wave composition that has been applied to the hair. The oxidizing system of the invention is used after applying to hair an aqueous composition that serves to reduce disulfide bonds of the hair by the action of an organic mercaptan such as thioglycolic or thiolactic acid or its salts or bisulfites or phosphines. The ascorbic acid composition of the present invention is applied subsequently to re-oxidize the keratin disulfide bonds and thus to permanently reconfigure the hair.

Another aspect of the present invention is a method for using the inventive oxidizing system for the oxidation dyeing of hair without bleaching. The hair is dyed by applying a dye composition to the hair and then developing oxidative color, without bleaching, at acidic, neutral or alkaline pH using the oxidizing system of the invention, wherein the oxidizing system is added to the dye composition at the time of use either: (i) separately from the dye composition at the same time that the dyeing composition is applied to the hair or (ii) sequentially with the dye composition.

Yet another aspect of the present invention is a multi-compartment device or permanent wave or dyeing kit or any other multi-compartment packaging system, a first compartment of which contains either a permanent wave composition or a hair dye composition and a second compartment of which contains the oxidizing system as defined above.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

DETAILED DESCRIPTION

Reference will now be made in detail to the presently preferred embodiments of the present invention.

The oxidizing system of the present invention is useful for both the neutralization of a permanent wave and the development of an oxidation hair color because it does not redden or bleach the hair while quenching a permanent wave process or while developing hair color composition. Thus, the hair stylist has better control of the end results.

Using the inventive system, keratin sulfide is effectively transformed to keratin disulfide, without the increase in cysteic acid that occurs when either hydrogen peroxide or bromate are used. When the inventive oxidizing system is employed, no discoloration of hair due to the destruction of the melanin pigment in keratin occurs as it does when hydrogen peroxide comes in contact with hair. These observations indicate that a peroxide-free oxidant is formed in the inventive system.

Overall, when used in permanent hair waving, the novel oxidizing system demonstrates the following advantages, as compared to the conventional hydrogen peroxide (2% $H_2O_2$, pH 3):

Provides for a greater recovery of disulfide bonds

Prevents an excessive formation of cysteic acid

Sustains the tensile strength of the processed hair

Preserves the natural hair pigment

Provides for protection of oxidative hair color during permanent wave process.

When used in oxidation hair coloring, the present invention allows for development of a no-lift hair color, with less oxidative damage to the hair.

An additional aspect of the invention is that the oxidizing system can develop superoxygenated water solutions at will. Without being bound by theory, the inventors have found that when the presently claimed components of ascorbic acid and the metal ion are mixed into water and then the oxidizing agent is added, there is an apparent disappearance of all oxygen from the water followed by the increase of dissolved oxygen much in excess of that which is normally dissolved in water and without the bubbling of this excess oxygen from the water. This appearance of the superoxygenated water and lack of bubbling suggests that the action of the inventive system is not the chemistry of a metal-catalyzed degradation of peroxide but that there is another agent present when the components of the inventive system come together.

While the most preferred use of the present invention is in hair dyeing and permanent waving compositions, superoxygenated solutions as described above can also serve as oxygen suppliers to skin for personal care or act as a type of antiseptic to anaerobic bacteria.

Thus, the present invention is directed to an oxidizing system comprising: ascorbic acid, at least one metal ion and an oxidizing agent capable of generating an oxidizing potential of from about 100 to about 500 millivolts at a pH ranging from about 2 to about 10. Preferably, the oxidizing agent is capable of generating an oxidizing potential of at least about 150 millivolts at a pH ranging from about 7 to about 9. The ascorbic acid and the oxidizing agent are preferably present in a molar ratio ranging from about 1:2 to about 1:10, more preferably in a molar ratio of about 1:4 mol/mol.

The amount of the at least one metal ion preferably ranges from about 3 ppm to about 30 ppm. Preferably, the at least one metal ion is present in an amount of from about 15 to about 20 ppm.

Metal ions useful in acting as catalysts in the oxidizing system of the invention include copper, iron, manganese, magnesium, and mixtures thereof. Preferably, these metal ions are $Cu^{2+}$, $Fe^{3+}$, $Mn^{2+}$, or $Mg^{2+}$. More preferably, the at least one metal ion is $Cu^{2+}$.

The source of the metal ions can be, but is not limited to, a metallo-sugar complex, or a complex of metal ions and other agents capable of complexation with metal ions such as peptides, amino acids and proteins. Useful metallo-sugar complexes include copper (II) gluconate, ferric (III) gluconate, manganese (II) gluconate, or magnesium (II) gluconate, or other sugars such as lactose, maltose, or sucrose. Preferably, the source for the metal ions to be used in the invention is copper (II) gluconate.

Other water-soluble salts of these divalent metal ions are also useful, such as the sulfate, ammonium, sodium, and potassium salts of these ions.

The oxidizing agent used in the present invention must be capable of generating an oxidizing potential, also called an electromotive potential or Emv, of from about 100 to about 500 millivolts at a pH ranging from about 2 to about 10. The preferred Emv is at least about 150 millivolts. It is also preferable for the oxidizing agent to be capable of achieving a rapid release of oxygen. The oxidizing agents useful in the present invention include but are not limited to alkali metal salts, ammonium salts, phosphate salts of perborate, percarbonate, persulfate, and peroxide, and mixtures of any of these oxidizing agents. Preferably, the oxidizing agent is sodium perborate, sodium percarbonate, potassium perborate, urea peroxide, or a mixture thereof. More preferably, the oxidizing agent is sodium perborate. When sodium perborate is used, it has been found that while it is not soluble in the ascorbic acid or the metal ion solution alone, it is very soluble in the combination of ascorbic acid and metal ion, particularly copper.

In a preferred embodiment of the novel oxidizing system of the present invention, the oxidizing agent is sodium perborate and the metal ion is $Cu^{2+}$. In this preferred system, the ratio of ascorbic acid:sodium perborate is 1:4, mol/mol, e.g., 2 g ascorbic acid (0.01 mol) and 4 g sodium perborate monohydrate (0.04 mol), and the copper ion is present in the form of copper gluconate in an amount of 0.014 g (20 ppm $Cu^{2+}$).

The pH of the oxidizing system of the invention ranges from about 2 to about 10. Preferably, the pH ranges from about 5 to about 10. More preferably, the pH ranges from about 7.5 to about 10.

The present invention may be used in the form of a kit. Thus, the inventive composition may be packaged in a multi-compartment device or permanent wave or dyeing kit or any other multi-compartment packaging system. In this device, kit, or packaging system, a first compartment contains either a permanent wave composition or a hair dye composition and a second compartment contains the oxidizing system as defined above.

The present invention also includes methods for the use of the oxidizing system described above. The novel oxidizing system of the invention can be used to develop oxidative color on hair without bleaching. Also, the oxidizing system of the invention is used in a method for quenching a permanent wave lotion that has been applied to human hair. These methods are similar in that they include the steps of applying a dyeing or permanent waving composition to hair and then applying, at the time of use, either (i) separately from the dyeing or waving composition at the same time that the dyeing or waving composition is applied to the hair or (ii) sequentially with the dyeing or waving composition, an oxidizing system comprising ascorbic acid, at least one metal ion, and an oxidizing agent capable of generating an oxidizing potential of from about 100 to about 500 millivolts at a pH ranging from about 2 to about 10.

With respect to dyeing, any dye composition known to the skilled artisan may be employed, such as those described in U.S. Pat. Nos. 4,226,595, 4,277,244, and 5,138,941.

With respect to the permanent wave process, any permanent wave lotion known to the skilled artisan may be employed. For example, ammonium thioglycolate, ammonium thiolactate, glyceryl monothioglycolate, or a combination thereof that may also contain thiolactic or thioglycolic acid at a pH ranging from 5 to 11, are permanent wave lotions known in the art. Such lotions are described by L. J. Wolfram, "The Reactivity of Human Hair: A Review," in *Hair Research: Status and Future Aspects,* C. E. Orfanos, W. Montagna, and G. Stuftgen, ed., Springer-Verlag publ., Germany 1981.

The invention will be illustrated by, but is not intended to be limited to, the following examples.

EXAMPLE 1: Comparative Example

The following solutions were prepared.

| Solution A (inventive) | |
|---|---|
| $Cu^{2+}$ | 20 ppm |
| ascorbic acid | 2 g |
| sodium perborate monohydrate | 4 g |
| water | q.s. 100% |
| Solution B (comparative) | |
| $Cu^{2+}$ | 20 ppm |
| ascorbic acid | 2 g |
| sodium perborate monohydrate | 0 |
| water | q.s. 100% |

Solutions A and B were compared and the following results obtained:

TABLE 1

| | SOLUTION A (inventive) | SOLUTION B (comparative) |
|---|---|---|
| Oxidizing potential | +147.2 mv | −300 mv |
| $pO_2$ | 90.3 mg/l | 0 |

Clearly, the solution containing the oxidizing agent sodium perborate showed a much higher oxidizing potential (Emv) and a much higher amount of dissolved oxygen ($pO_2$).

EXAMPLE 2: Test Curl Test Tube (TTTC) Determination

Twelve hair fibers of normal brown hair and twelve fibers of tinted brown hair were each glued together at the root end. Each swatch was dampened with tap water and wound on a 7 mm perm rod under moderate tension. Ammonium thioglycolate (ATG) was used as the permanent wave composition.

Six swatches of normal hair and six swatches of tinted hair per test were processed in a polystyrene bath (13 cm×13 cm). Reforming lotion was applied with a 5 mL polyethylene disposable pipette, 2 mL of solution per rod. Half of each set of samples were treated with a reforming solution containing the oxidizing system of the present invention. The other half were treated with a re-forming solution containing as oxidizer conventional hydrogen peroxide, i.e., 2% $H_2O_2$, pH 3.

After each swatch was thoroughly saturated with the solution, any excess of the reforming lotion was removed from the bath; the bath was covered with Reynolds 910 film and maintained at room temperature for 20 min. As a rinse step, 150 mL of deionized water was added to the swatches for 5 min; the rinse water was decanted from the bath, and each swatch was paper-blotted. A neutralizing (bonding) lotion was applied with a polyethylene pipette to each swatch for 5 min, 2 mL of solution per rod.

As a final rinse step, another 150 mL of d/i water was added to the swatches for 5 min, decanted, and the swatches were paper-blotted.

After processing, each swatch was unwound from the rod, and the length and the diameter of the wet curl were measured. These data were supplemented with the length of the dried curls. The results were averaged for the six swatches and presented in a table form. The results were analyzed for statistical significance using One Way Anova/Jandel Sigma Stat Version 2.0.

The results for normal brown hair and the hair after an oxidative damage are presented in Table 2. In all cases, the novel ascorbic acid neutralizer resulted in the formation of a curl pattern that was comparable to that obtained with the conventional hydrogen peroxide (2% $H_2O_2$, pH 3).

TABLE 2

| Hair Type/Treatment | Curl Length, cm | Curl Diameter, mm |
|---|---|---|
| 1. Normal brown hair before perming (15.8 cm). Waving lotion: 10% ATG, pH 8.5 ($NH_4OH$), 30 min. Neutralization - 5 min Perm Neutralizers: | | |
| 2% $H_2O_2$, pH3 | 6.13 ± 0.14 cm | 9.60 ± 0.70 mm |
| 2% $H_2O_2$, pH9 | 6.46 ± 0.23 cm | 10.10 ± 0.10 mm |
| 2% Ascorbic acid, 4% $NaBO_3$ $H_2O$, 20 ppm Cu, pH 8.7 | 5.51 ± 0.23 cm | 8.50 ± 0.49 mm |
| 2. Brown hair processed with Color Gel Clear/20 Volume before perming (15.8 cm). Waving lotion: 8% ATG, pH 8.5 (NH4OH), 30 min. Neutralization - 5 min Perm Neutralizers: | | |
| 2% $H_2O_2$, pH3 | 6.58 ± 0.18 cm | 10.00 ± 0.70 mm |
| 2% $H_2O_2$, pH9 | 7.28 ± 0.22 cm | 11.00 ± 0.10 mm |
| 2% Ascorbic acid, 4% $NaBO_3$ $H_2O$, 20 ppm Cu, pH 8.7 | 6.50 ± 0.40 cm | 10.50 ± 0.50 mm |

EXAMPLE 3: Tensile Strength

Tensile strength of hair was measured using an Instron 1122. Tensile strength is measured as "Work 20%," i.e., work required to extend the hair to 20% of its length. The measurements were conducted at 20° C. and 50% RH, at a rate of 100 mm/min. The tests were performed on 32 fibers per treatment. The averaged results were compared between the treatment using the pairwise multiple comparison procedures based on Student-Newman-Keuls method or Kruskal-Wallis One Way Analysis of Variance on Ranks (One Way Anova for SigmaStat Version 2.0).

The tensile strength data of normal and oxidatively damaged hair after three consecutive perms are presented in Table 3 (below, after Example 4). After three perms with the novel neutralizer, the tensile strength of the normal hair had decreased by 1.4%, and of the oxidatively damaged hair—by 8%. In contrast, when the hair was permed three times using the conventional hydrogen peroxide, the tensile strength of the normal hair dropped by 40%, and of the oxidatively damaged hair—by 50%.

EXAMPLE 4: Amino Acid Analysis of Hair Hydrolyzates

A specific amount of hair (0.500–0.900 mg) was weighed on a Mettler AT 20 microbalance. The weighed sample was placed in a 6 mL prescored glass tube, and 2 mL of 6N HCl were added. The tube was sealed under vacuum and maintained at 110° C. for 24 h in a multi-block heater (Lab-Line Instruments, Inc.). Next, the hydrochloric acid was removed using a Speed Vac Plus SC 210 (Savant) equipped with a Refrigerated Condensation Trap (Savant).

The dry hydrolysate was dissolved in Na-S High Performance Amino Acid Sample Dilution Buffer (Beckman) at a ratio of 0.38 mL Na-S per 0.1 mg of dry hair. To remove particulate contamination, the dissolved hydrolyzate was filtered into a 10 mL plastic capped test tube using a 10 mL disposable syringe (Plastipak) Luer locked to a Swinney holder with 0.2 micron filter paper. The filtered hydrolyzate was loaded into sample coils and analyzed in accordance with the Instruction Manual for High Performance Amino Acid Analyzers (Beckman, Series 6300).

The amino acid composition of normal and oxidatively damaged hair after three consecutive perms are presented in Table 3. The half-cystine content indicates the amount of disulfide bonds recovered after three consecutive perms. The cysteic acid content implies the irreversible damage to the hair due to over-oxidation. The higher the cysteic acid content, the more damage that has been done.

Both in the normal and the oxidatively damaged hair, the use of the novel ascorbate neutralizer resulted in a higher recovery of the disulfide bonds and a lower formation of cysteic acid.

TABLE 3

Tensile Strength and Amino Acid Analysis of Hair after 3 Consecutive Perms

| Hair Type/Treatment | Work 20% 10, MJ/m2 | Half-Cystine Mole % | Cysteic Acid Mole % |
|---|---|---|---|
| 1. Normal brown hair, no perm Waving lotion: 8% ATG, pH 8.5 ($NH_4OH$), 30 min. Neutralization - 5 min Perm Neutralizers: | 11.1 ± 2.16 | 16.03 ± 0.24 | 0.28 ± 0.06 |
| 2% $H_2O_2$, pH 3 | 6.77 ± 1.32 | 12.79 ± 0.02 | 1.61 ± 0.05 |
| 2% $H_2O_2$, pH 9 | 6.90 ± 1.21 | 12.30 ± 0.01 | 3.03 ± 0.01 |
| 2% Ascorbic acid, 4% $NaBO_3$ $H_2O$, 20 ppm Cu, pH 8.7 | 11.03 ± 1.82 | 14.13 ± 0.03 | 1.04 ± 0.01 |
| 2. Brown hair processed with Color Gel Clear/20 Volume (15.8 cm). No perm - control Waving lotion: 8% ATG, pH 8.5 (NH4OH), 30 min. Neutralization - 5 min Perm Neutralizers: | 10.92 ± 2.69 | 14.52 ± 0.13 | 1.35 ± 0.03 |
| 2% $H_2O_2$, pH 3 | 5.89 ± 0.80 | 11.50 ± 0.13 | 2.25 ± 0.01 |
| 2% $H_2O_2$, pH 9 | 5.35 ± 0.95 | 11.14 ± 0.03 | 3.07 ± 0.01 |
| 2% Ascorbic acid, 4% $NaBO_3$ $H_2O$, 20 ppm Cu, pH 8.7 | 10.12 ± 2.19 | 12.96 ± 0.02 | 1.37 ± 0.01 |

EXAMPLE 5: Effect on Color of Natural Pigmented Hair

A discoloration may occur in natural pigmented hair subjected to reactive chemical processing such as permanent waving, dyeing, or bleaching. The novel oxidative ascorbate/perborate/copper system was compared with hydrogen peroxide with respect to discoloration in natural pigmented hair (dark brown, light brown, and blonde hair, respectively) caused by permanent waving and bleaching.

The following oxidative solutions were used as neutralizers in permanent waving of pigmented hair: 1) 2% ascorbic acid, 5% sodium perborate monohydrate, 20 ppm Cu; 2) 2% hydrogen peroxide at pH 3; and 3) 2% hydrogen peroxide at pH 9. In order to more clearly distinguish between the degree of discoloration observed for different systems, the permanent waving tests were repeatedly performed on the same hair swatches up to 5 times (Table 4).

To study the bleaching effect, natural pigmented hair was treated up to 18 h with 1) 2% ascorbic acid/5% $NaBO_3H_2O$/ 20 ppm Cu, 2) 2% $H_2O_2$, pH 3, and 3) 2% $H_2O_2$, pH 9, respectively (Table 5).

The change in hair color was evaluated based on L, a, b values taken using a Datacolor International Spectrophotometer. Here, L value corresponds to the level of darkness of the hair (higher L values correspond to lighter hair); a value corresponds to red shade, and b—to yellow shade.

For all three hair types, the hydrogen peroxide resulted in the development of significantly higher a and b values after the treatments, with the discoloration being more pronounced at pH 9 than at pH 3. Bleaching of hair involves the formation of yellow color, thus the b value increased for hair treated with hydrogen peroxide. Dark hair also experiences an increase in red tones, hence the increased a values for the hair treated with hydrogen peroxide, particularly for the dark brown and light brown hair. The ascorbate-based solution caused little discoloration in the three hair types.

TABLE 4

Effect of Multiple Perm Treatments on Color of Natural Hair Waving Lotion: 10% ATG, pH 10, 20 min: Neutralization - 5 mm

| Hair Type/# of Perm Treatments | L | a | b |
|---|---|---|---|
| 1. Dark Brown Hair Level 3, | | | |
| No perm - Control | 19.95 ± 0.14 | 2.58 ± 0.26 | 2.18 ± 0.33 |
| Neutralizer - 2% $H_2O_2$, pH 3 | | | |
| 1 Perm | 21.03 ± 0.24 | 2.83 ± 0.45 | 2.36 ± 0.22 |
| 3 Perms | 20.38 ± 0.38 | 3.50 ± 0.20 | 2.86 ± 0.17 |
| 5 Perms | 21.92 ± 0.88 | 4.28 ± 0.48 | 4.06 ± 0.13 |
| Neutralizer - 2% $H_2O_2$, pH 9 | | | |
| Perm | 20.43 ± 0.91 | 3.81 ± 0.03 | 3.45 ± 0.15 |
| 3 Perms | 20.84 ± 0.77 | 4.39 ± 0.26 | 4.10 ± 0.30 |
| 5 Perms | 21.98 ± 0.40 | 5.09 ± 0.12 | 4.94 ± 0.20 |
| Neutralizer - 2% ascorbic acid 5% $NaBO_3H_2O$, 20 ppm Cu, pH 8.7 | | | |
| 1 Perm | 22.12 ± 0.74 | 2.47 ± 0.25 | 1.64 ± 0.28 |
| 3 Perms | 21.57 ± 0.58 | 2.48 ± 0.25 | 1.49 ± 0.10 |
| 5 Perms | 22.37 ± 1.37 | 2.68 ± 0.23 | 1.93 ± 0.25 |
| 2. Light Brown Hair, Level 5 | | | |
| No perm - Control | 25.81 ± 0.65 | 5.56 ± 0.36 | 8.32 ± 0.90 |
| Neutralizer - 2% $H_2O_2$, pH 3 | | | |
| 1 Perm | 26.20 ± 1.31 | 5.76 ± 0.11 | 8.45 ± 0.27 |
| 3 Perms | 28.22 ± 0.80 | 6.59 ± 0.12 | 9.93 ± 0.49 |
| 5 Perms | 28.60 ± 1.41 | 6.89 ± 0.02 | 10.63 ± 0.33 |
| Neutralizer - 2% $H_2O_2$, pH 9 | | | |
| 1 Perm | 26.80 ± 0.41 | 6.50 ± 0.11 | 9.80 ± 0.19 |
| 3 Perms | 28.09 ± 0.51 | 7.24 ± 0.06 | 11.60 ± 0.19 |
| 5 Perms | 29.70 ± 1.58 | 8.29 ± 0.14 | 13.32 ± 0.34 |
| Neutralizer - 2% ascorbic acid 5% $NaBO_3H_2O$, 20 ppm Cu, pH 8.7 | | | |
| 1 Perm | 28.13 ± 0.69 | 5.50 ± 0.87 | 8.06 ± 0.32 |
| 3 Perms | 28.42 ± 1.44 | 5.87 ± 0.83 | 8.23 ± 0.56 |
| 5 Perms | 29.37 ± 0.32 | 5.91 ± 0.06 | 8.64 ± 0.29 |
| 3. Blonde hair, level 7 | | | |
| No perm - Control | 36.77 ± 1.52 | 7.06 ± 0.32 | 15.17 ± 0.17 |
| Neutralizer - 2% $H_2O_2$, pH 3 | | | |
| 1 Perm | 36.12 ± 0.69 | 7.02 ± 0.08 | 15.43 ± 0.43 |
| 3 Perms | 38.27 ± 1.01 | 8.03 ± 0.09 | 17.31 ± 0.08 |
| 5 Perms | 39.34 ± 0.78 | 8.30 ± 0.49 | 18.22 ± 0.40 |
| Neutralizer - 2% $H_2O_2$, pH 9 | | | |
| 1 Perm | 37.55 ± 0.24 | 7.43 ± 0.20 | 17.07 ± 0.24 |
| 3 Perms | 39.30 ± 1.13 | 8.34 ± 0.45 | 18.29 ± 0.18 |
| 5 Perms | 39.95 ± 1.21 | 9.53 ± 0.36 | 19.63 ± 0.30 |
| Neutralizer - 2% ascorbic acid 5% $NaBO_3H_2O$, 20 ppm Cu, pH 8.7 | | | |
| 1 Perm | 36.06 ± 0.64 | 6.73 ± 0.36 | 13.91 ± 0.50 |
| 3 Perms | 36.54 ± 0.31 | 7.31 ± 0.14 | 15.03 ± 0.35 |
| 5 Perms | 37.18 ± 0.75 | 7.34 ± 0.11 | 15.06 ± 0.81 |

TABLE 5

Effect of Oxidizing Solutions on Color of Natural Hair 90 min soaking in an excess of an oxidizing solution at room temperature

| Hair Type/Oxidizing Solution | L | a | b |
|---|---|---|---|
| Dark Brown Hair Level 3, | | | |
| No treatment - control 90 min Soaking in: | 19.95 ± 0.14 | 2.58 ± 0.26 | 2.18 ± 0.33 |
| 2% $H_2O_2$, pH 3 | 21.88 ± 0.64 | 3.61 ± 0.15 | 3.10 ± 0.36 |
| 2% $H_2O_2$, pH 9 | 23.73 ± 0.45 | 6.54 ± 0.25 | 7.40 ± 0.36 |
| 2% ascorbic acid, 5% $NaBO_3$ $H_2O$, 20 ppm Cu, pH 8.7 | 21.06 ± 0.64 | 3.01 ± 0.15 | 2.38 ± 0.23 |
| Light Brown Hair Level 5, | | | |
| No treatment - control 90 mm Soaking in: | 25.81 ± 0.65 | 5.56 ± 0.36 | 8.32 ± 0.90 |
| 2% $H_2O_2$, pH 3 | 27.21 ± 0.54 | 6.95 ± 0.25 | 10.29 ± 0.60 |
| 2% $H_2O_2$, pH 9 | 32.05 ± 1.11 | 8.67 ± 0.51 | 14.48 ± 0.21 |
| 2% ascorbic acid, 5% $NaBO_3$ $H_2O$, 20 ppm Cu, pH 8.7 | 28.30 ± 0.36 | 6.27 ± 0.19 | 9.21 ± 0.65 |
| Blonde Hair Level 7, | | | |
| No treatment - control 90 mm Soaking in: | 36.77 ± 1.52 | 7.06 ± 0.32 | 15.17 ± 0.17 |
| 2% $H_2O_2$, pH 3 | 38.55 ± 0.88 | 7.75 ± 0.24 | 16.74 ± 0.46 |
| 2% $H_2O_2$, pH 9 | 42.78 ± 0.44 | 9.16 ± 0.26 | 21.54 ± 0.56 |
| 2% ascorbic acid, 5% $NaBO_3$ $H_2O$, 20 ppm Cu, pH 8.7 | 38.85 ± 0.93 | 7.34 ± 0.36 | 15.58 ± 0.48 |

EXAMPLE 6: Protection of Oxidative Color in Hair during Permanent Wave Process

Dyed blonde hair was processed with an 8% ATG waving lotion, and neutralized with 2% hydrogen peroxide (pH 3), or the inventive solution (2% ascorbic acid, 4% $NaBO_3$ $H_2O$, 20 ppm Cu), respectively.

Color retention in the hair after perm was assessed based on L, a, b values, on the one hand, and on visual evaluation by a panel of trained colorists, on the other hand. The results are presented in Table 6 and 6a. The swatches treated with the inventive composition underwent less change in L and b values, when compared to the hydrogen peroxide swatches. Visually, the swatches treated with the inventive composition retained more vibrant color that appeared to be closer to the non-treated control, as compared to the swatches neutralized with the hydrogen peroxide.

TABLE 6

Color Retention in Dyed Natural Blonde Hair: L, a, b values
Reforming Lotion: 20 min; Neutralizer: 7 min

| NEUTRALIZER | L | a | b |
|---|---|---|---|
| Control - no perm | 29.00 ± 0.93 | 15.89 ± 0.65 | 13.96 ± 1.09 |
| Invention oxidizing system | 30.45 ± 0.88 | 14.96 ± 0.08 | 14.11 ± 0.6 |
| 2% $H_2O_2$, pH 3 | 33.10 ± 0.95 | 15.84 ± 0.46 | 16.97 ± 0.56 | a. Color Retention in Dyed Natural Blonde Hair; Panel Evaluation

| PANELIST ## | CONTROL | INVENTIVE | 2% $H_2O_2$, pH 3 |
|---|---|---|---|
| 1 | .64 | .46* | .43 |
| 2 | .64 | .45* | .43 |
| 3 | .54 | .45* | .34 |
| 4 | .54 | .45* | .34 |
| 5 | .64 | .43* | .34 |

*samples that were visually evaluated as closest to control in tone
.xy-x primary reflect tone; y-secondary reflect tone
3-gold; 4-copper; 5-mahogany; 6-red

EXAMPLE 7: Color Development in Natural White Hair from Oxidative Dyes

The optimum inventive composition, i.e., 2% ascorbic acid, 4% $NaBO_3$ $H_2O$, 20 ppm Cu, was used to develop oxidative color in natural white hair from several primary/coupler combinations (Table 7).

TABLE 7

Color Development in Natural White Hair with Some Oxidative Dyes
Using the Novel Oxidizing System as Color Developer
Dye Solution:Oxidizing System = 1:1, v/v

| Primary/Coupler 1:1, mol/mol, 5 × $10^3$M (1.5% $NH_3$) | L | a | b |
|---|---|---|---|
| PPD*/Resorcinol | 52.93 | 5.82 | 17.53 |
| PPD/MAP | 0.47 | 12.99 | 1.04 |
| PPD/OAJ | 29.88 | −0.75 | −12.28 |
| PPD/PAOC | 37.53 | 19.88 | 5.41 |

*PPD = paraphenylene diamine
MAP = m-aminophenol
OAJ = 2-methyl-5-hydroxyethylaminophenol
PAOC = 4-amino-o-cresol

EXAMPLE 8: Determination of Preferred Ratio of Components

Table 8 shows the chemistry of systems prepared with different component ratios and their corresponding electrochemical parameters. Also shown are the disulfide bond recovery and the tensile strength of the hair that was permed three times using these compositions as perm neutralizers. The results of these experiments allowed the determination of a preferred composition of the oxidizing system for a permanent wave process as 2% ascorbic acid, 4% sodium perborate monohydrate, and 20 ppm Cu.

TABLE 8

| Reaction at 5 min | Hair after 3 Perms Half-Cystine Mole % | Work 20% x10, MJ/m2 |
|---|---|---|
| Natural hair - No perm | 16.03 ± 0.24 | 11.18 ± 2.16 |

1. Effect of Copper Concentration: 2% Ascorbic acid 4% Sodium Perborate Monohydrate with

| | pH | Emv | $pO_2$, mg/L | T °C. | Hair After 3 Perms Half-Cystine Mole % | Work 20% x10, MJ/m2 |
|---|---|---|---|---|---|---|
| 0 ppm Cu | 8.9 | −75.2 | 0.12 | 23.2 | 12.83 ± 0.05 | 6.97 ± 1.53 |
| 5 ppm Cu | 8.6 | +145.1 | 30.2 | 33.5 | 13.63 ± 0.09 | 8.91 ± 1.88 |
| 10 ppm Cu | 8.6 | +146.3 | 55.6 | 34.1 | 13.68 ± 0.08 | 10.21 ± 1.95 |
| 20 ppm Cu | 8.6 | +147.2 | 90.3 | 35.3 | 14.13 ± 0.03 | 11.03 ± 1.82 |

2. Effect of Sodium Perborate Monohydrate Concentration: 2% Ascorbic acid 20 ppm Cu with

| $NaBO_3.H_2O$ | pH | Emv | $pO_2$, mg/L | T °C. | Hair After 3 Perms Half-Cystine Mole % | Work 20% x10, MJ/m2 |
|---|---|---|---|---|---|---|
| 2% | 8.9 | +147.2 | 2.2 | 32.1 | 12.60 ± 0.56 | 7.89 ± 2.21 |
| 3% | 8.7 | +148.1 | 72.3 | 33.2 | 13.29 ± 0.14 | 8.71 ± 2.77 |
| 4% | 8.6 | +149.2 | 85.7 | 34.5 | 14.13 ± 0.03 | 11.03 ± 1.82 |
| 5% | 8.5 | +150.3 | 84.5 | 34.5 | 12.85 ± 0.01 | 7.63 ± 1.39 |
| 6% | 8.4 | ±151.2 | 90.1 | 34.5 | 12.63 ± 0.01 | 6.71 ± 1.37 |

EXAMPLE 9: Superoxygenated Solutions 2 g of ascorbic acid, 4 g sodium perborate monohydrate and 0.014 g copper gluconate (20 ppm $Cu^{2+}$) were dissolved in 93.98 g of deionized water to produce a solution that, after 5 minutes of reaction, developed a concentration of dissolved oxygen of 90 mg/l. The solution maintained this concentration of dissolved oxygen for at least 30 minutes.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. An oxidizing system for reforming cystine and for developing oxidative color in keratinous fibers comprising:
    ascorbic acid,
    an oxidizing agent capable of generating an oxidizing potential of from 100 to 500 millivolts in said system, wherein said ascorbic acid and said oxidizing agent are included in said system in a ratio effective for reforming cystine during a permanent wave or oxidation dyeing process without excessive formation of cysteic acid to weaken said keratinous fibers, said ratio of ascorbic acid:oxidizing agent ranging from 1:2 to 1:10, and
    at least one metal ion in a catalytically effective amount, wherein said system has a pH ranging from 2 to 10, and further wherein said system does not bleach or discolor said keratinous fibers.

2. An oxidizing system according to claim 1, wherein said oxidizing agent is an alkali metal salt or an ammonium salt of perborate, percarbonate, persulfate, or peroxide, or a mixture thereof.

3. An oxidizing system according to claim 1, wherein said oxidizing agent is sodium perborate, sodium percarbonate, potassium perborate, or urea peroxide.

4. An oxidizing system according to claim 3, wherein said oxidizing agent is sodium perborate.

5. An oxidizing system according to claim 1, wherein said at least one metal ion is selected from copper ions, iron ions, or mixtures thereof.

6. An oxidizing system according to claim 5, wherein said at least one metal ion is $Cu^{2+}$ or $Fe^{3+}$.

7. An oxidizing system according to claim 6, wherein said at least one metal ion is $Cu^{2+}$.

8. An oxidizing system according to claim 1, wherein said at least one metal ion is generated from a complex of metal ions and at least one agent capable of complexation with metal ions.

9. An oxidizing system according to claim 8, wherein said at least one agent is a sugar, a peptide, an amino acid, or a protein.

10. An oxidizing system according to claim 9, wherein said sugar is glucose, sucrose, lactose, or maltose.

11. An oxidizing system according to claim 10, wherein said complex is a metallo-sugar complex selected from copper (II) gluconate or ferric (III) gluconate.

12. An oxidizing system according to claim 11, wherein said metallo-sugar complex is copper (II) gluconate.

13. An oxidizing system according to claim 1, wherein said ascorbic acid and said sodium perborate are present in a ratio of about 1:4 mol/mol.

14. An oxidizing system according to claim 1, wherein said at least one metal ion is present in an amount of from 3 to 30 ppm.

15. An oxidizing system according to claim 14, wherein said at least one metal ion is present in an amount of 15–20 ppm.

16. An oxidizing system according to claim 1, wherein the pH of said oxidizing system ranges from 5 to 10.

17. An oxidizing system according to claim 16, wherein the pH of said oxidizing system ranges from 7.5 to 10.

18. An oxidizing system according to claim 1, wherein said oxidizing potential is at least 150 millivolts.

19. An oxidizing system for reforming cystine and for developing oxidative color in keratinous fibers comprising:
    ascorbic acid,
    an oxidizing agent capable of generating an oxidizing potential of from 100 to 500 millivolts in said system, wherein said ascorbic acid and said oxidizing agent are included in said system in a ratio of ascorbic acid:oxidizing agent ranging from 1:2 to 1:10, and
    at least one metal ion in an amount ranging from 5 ppm to 30 ppm,
    wherein said system has a pH ranging from 2 to 10.

* * * * *